United States Patent [19]

Schaper et al.

[11] 4,212,773
[45] Jul. 15, 1980

[54] PERFUMERY COMPOSITIONS WITH TRIMETHYL-TETRAHYDROPYRAN-2-ONES

[75] Inventors: Ulf-Armin Schaper, Düsseldorf; Klaus Bruns, Krefeld-Traar, both of Fed. Rep. of Germany

[73] Assignee: Henkel Kommanditgesellschaft auf Aktien (Henkel KGaA), Düsseldorf-Holthausen, Fed. Rep. of Germany

[21] Appl. No.: 29,651

[22] Filed: Apr. 13, 1979

[30] Foreign Application Priority Data

Apr. 26, 1978 [DE] Fed. Rep. of Germany ....... 2818244

[51] Int. Cl.$^2$ .......................... C11B 9/00; A61K 7/46
[52] U.S. Cl. ..................... 252/522 R; 252/174.11; 252/108; 252/173; 252/368; 424/40; 424/59; 424/65; 424/69; 424/76
[58] Field of Search .......................... 252/522

[56] References Cited

U.S. PATENT DOCUMENTS

| | | | |
|---|---|---|---|
| 3,278,557 | 10/1966 | Chibnik | 252/522 R |
| 3,880,882 | 4/1975 | Story et al. | 252/522 R |
| 3,996,170 | 12/1976 | Shuster et al. | 252/522 R |

OTHER PUBLICATIONS

Karl-Wilhelm Rosenmund et al., Chem. Berichte, 94 2406, 1961.
Beilstein E III/IV 17, 4227.
Chem. Ab. 34:4863, 1960.

Primary Examiner—Veronica O'Keefe
Attorney, Agent, or Firm—Hammond & Littell, Weissenberger and Muserlian

[57] ABSTRACT

A perfumery composition consisting essentially of from 1% to 50% by weight of a trimethyl-tetrahydropyran-2-one selected from the group consisting of (1) 4,6,6-trimethyl-tetrahydropyran-2-one of the formula

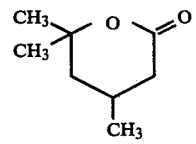

(2) 4,4,6-trimethyl-tetrahydropyran-2-one of the formula

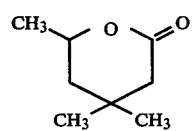

and
(3) mixtures of (1) and (2), and the remainder customary constituents of perfumery compositions; as well as the method of imparting a pleasing odor utilizing said trimethyl-tetrahydropyran-2-ones.

6 Claims, No Drawings

… … …

PERFUMERY COMPOSITIONS WITH TRIMETHYL-TETRAHYDROPYRAN-2-ONES

BACKGROUND OF THE INVENTION

The present invention relates to perfumery compositions containing certain trimethyl-tetrahydropyran-2-ones and method of imparting a pleasant odor to industrial products employing the same.

OBJECTS OF THE INVENTION

An object of the present invention is the development of a perfumery composition with a characteristic fragrance with a walnut nuance.

A further object of the present invention is the development of a perfumery composition consisting essentially of from 1% to 50% by weight of a trimethyl-tetrahydropyran-2-one selected from the group consisting of
  (1) 4,6,6-trimethyl-tetrahydropyran-2-one of the formula

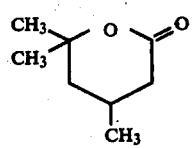

(2) 4,4,6-trimethyl-tetrahydropyran-2-one of the formula

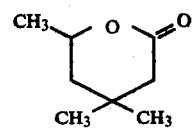

and
  (3) mixtures of (1) and (2),
and the remainder customary constituents of perfumery compositions.

A yet further object of the present invention is the development of a method of imparting a pleasing odor to a product comprising adding to said product from 0.05% to 5% by weight of the perfumery composition given above, as a scenting agent.

These and other objects of the invention will become more apparent as the description thereof proceeds.

DESCRIPTION OF THE INVENTION

We have now found that trimethyl-tetrahydropyran-2-ones of the formula

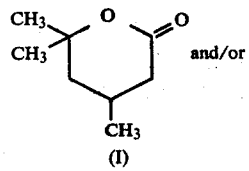 and/or 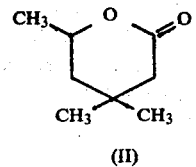
  (I)                             (II)

can be used in advantageous manner as perfumes in compositions for perfuming technical and cosmetic products.

More particularly, the present invention relates to a perfumery composition consisting essentially of from 1% to 50% by weight of a trimethyl-tetrahydropyran-2-one selected from the group consisting of
  (1) 4,6,6-trimethyl-tetrahydropyran-2-one of the formula

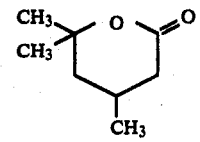

(2) 4,4,6-trimethyl-tetrahydropyran-2-one of the formula

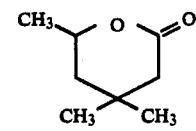

and
  (3) mixtures of (1) and (2),
and the remainder customary constituents of perfumery compositions.

The production of the compounds, which are known in the literature, is effected with good yields by oxidizing the corresponding trimethyl-cyclopentanones according to Bayer-Villiger by means of a peracid. Peracetic acid is the preferred peracid, but other organic or inorganic peracids can also be used. 4,6,6-Trimethyl-tetrahydropyran-2-one (I) is obtained by using 2,2,4-trimethyl cyclopentanone (Beilstein E III/IV 17, 4227). 4,4,6-Trimethyl-tetrahydropyran-2-one (II) is obtained by using 2,4,4-trimethyl-cyclopentanone (Chem. Ber. 94, 2406 [1961]) as a starting material. For the production of a technical product, a commercial mixture of about 60 parts by weight of 2,2,4-trimethyl-cyclopentanone and about 40 parts by weight of 2,4,4-trimethyl-cyclopentanone, known as trimethyl-cyclopentanone (TMCP-one) can be used. From this mixture, a 60:40 mixture of compounds (I) and (II) results.

The trimethyl-tetrahydropyran-2-ones according to the invention are valuable perfumes with a characteristic walnut note. They can be easily combined to novel and interesting odor nuances. Of the two products, 4,6,6-trimethyl-tetrahydropyran-2-one (I) is the more interesting and valuable product, with a mildly bitter typical walnut nuance, while 4,4,6-trimethyl-tetrahydropyran-2-one (II) has a more complex herbaceous nutty-to-methone nuance. The mixture of about 60 parts by weight of (I) and about 40 parts by weight of (II) still has the typical walnut nuance similar to (I). Preferably any mixture should have about 50% or more of 4,6,6-trimethyl-tetrahydropyran-2-one (I). Nothing is found in the known literature about these perfume properties and the possible use of the compounds in perfumes.

The trimethyl-tetrahydropyran-2-ones to be used as perfumes according to the invention can be mixed with other perfumes in various quantitative ratios to form new perfumery compositions. In general, the portion of the trimethyl-tetrahydropyran-2-ones to be used in the perfumery compositions according to the invention will vary between 1% and 50% by weight, related to the total perfumery composition. The remainder of the composition are conventional perfumery constituents.

Such compositions can be used directly as perfumes or, alternatively, can be used to perfume cosmetics, such as creams, lotions, toilet waters, aerosols, toilet soaps, and technical articles, such as detergents or cleansers, disinfectants and textile preparations.

Due to their typical walnut nuance, they are suitable as the sole perfumes in sunlight protecting preparations, such as suntan creams, suntan lotions, and suntan oils. When employed to impart an odor to products, the perfumery compositions are employed in amounts of from 0.05% to 5%, preferably 0.1% to 2% by weight.

The following examples will illustrate the subject of the invention, without limiting it, however, to these examples.

EXAMPLES

Preparation of 4,4,6-trimethyl-tetrahydropyran-2-one (I)

3.84 gm of 2,2,4-trimethyl-cyclopentanone were dissolved in 50 ml of chloroform and cooled in the ice bath. At 0° C., a solution of 0.2 gm of sodium acetate in 11.4 gm of a 40% aqueous peracetic acid was added. The reaction mixture was stirred for 18 hours at room temperature, then neutralized with a sodium hydrogen carbonate solution. The organic phase was separated, dried and concentrated. By distillation, 3.4 gm of 4,6,6-trimethyl-tetrahydropyran-2 -one (I) were recovered with the following characteristics:

B.P. 65° C. at 0.1 m bar
M.P. 29° to 30° C.
$n_D^{30} = 1.4470$
IR (oil) cm$^{-1}$: 1730, 1455, 1373, 1275, 1215, 1110, 990, 918, 785

| NMR (CD Cl$_3$) δ = | 1.03 ppm d (6 Hz) | 3 H |
| --- | --- | --- |
| | 1.4 ppm s | 3 H |
| | 1.42 ppm s | 3 H |
| | 1.6 ppm m | 2 H |
| | 2.05 ppm m | 1 H |
| | 2.6 ppm m | 2 H |

The odor nuance was typically walnut, fine mild-bitter.

Preparation of 4,4,6-trimethyl-tetrahydropyran-2-one (II)

Corresponding to the foregoing preparation, 3.81 gm of 2,4,4-trimethyl-cyclopentanone were reacted to give 3.6 gm of 4,4,6-trimethyl-tetrahydropyran-2-one (II). The compound has the following characteristics:

B.P. 65° C. at 0.13 m bar
$n_D^{20} = 1.4485$
IR (oil) cm$^{-1}$: 1735, 1455, 1385, 1310, 1240, 1178, 1140, 1047, 985, 970, 800.

| NMR (CD Cl$_3$) δ = | 1.05 ppm s | 3 H |
| --- | --- | --- |
| | 1.1 ppm s | 3 H |
| | 1.37 ppm d (6 Hz) | 3 H |
| | 1.63 ppm m | 2 H |
| | 2.3 ppm m | 2 H |
| | 4.5 ppm m (6 Hz, | 2 Hz) 1H |

The odor was herbaceous with a nutty to menthone nuance, more complex than (I).

Preparation of the 60:40 mixture of (I) and (II).

By the reaction of 315 gm of a commercial trimethyl cyclopentanone (TMCP-one by VEBA), following the foregoing preparations, 310 gm of a mixture of 4,6,6-trimethyl-tetrahydropyran-2-one (I) and 4,4,6-trimethyl-tetrahydropyran-2-one (II) were obtained in an approximate ratio of 3:2. The mixture has the following characteristics:

B.P. 62° C. at 0.47 m bar
$n_D^{20} = 1.4484$

The odor nuance was typically walnut, similar to the odor of (I).

EXAMPLE 1

Perfuming example of a sunlight protecting lotion

| | Parts by Weight |
| --- | --- |
| 4,6,6-Trimethyl-tetrahydropyran-2-one | 15 |
| Polyoxyethylene sorbitanoleate (Tween 80) | 60 |
| Isopropyl myristate | 20 |
| Propylene glycol | 20 |
| Sunlight protecting agent (Prosolal S8) | 50 |
| Distilled water | 835 |

EXAMPLE 2

Perfume composition for odorizing soaps and detergents

| | Parts by Weight |
| --- | --- |
| 4,6,6-Trimethyl-tetrahydropyran-2-one | 150 |
| p-tert.-Butylcyclohexyl acetate | 80 |
| Terpineol | 80 |
| Isobornyl acetate | 50 |
| Benzyl acetate | 50 |
| Galaxolide | 50 |
| Lavandin oil | 50 |
| Ionone | 50 |
| Cumarin | 40 |
| Benzyl salicylate | 40 |
| Cinnamic alcohol | 30 |
| Hydroxycitronellal | 30 |
| Peti grain oil | 30 |
| Ylang-oil | 30 |
| Galbanum oil synth. | 20 |
| Cyclamenaldehyde | 20 |
| Dihydromyrcenol | 20 |
| Anisaldehyde | 20 |
| Diethyl phthalate | 160 |

Instead of the 4,6,6-trimethyl-tetrahydropyran-2-one in the foregoing examples, a 60:40 mixture of 4,6,6-and 4,4,6-trimethyl-tetrahydropyran-2-one can also be used with equally good results.

The preceding specific embodiments are illustrative of the practice of the invention. It is to be understood, however, that other expedients known to those skilled in the art or disclosed herein may be employed without departing from the spirit of the invention or the scope of the appended claims.

We claim:

1. A perfumery composition consisting essentially of from 1% to 50% by weight of a trimethyl-tetrahydropyran-2-one selected from the group consisting of
   (1) 4,6,6-trimethyl-tetrahydropyran-2-one of the formula (2) 4,4,6-trimethyl-tetrahydropyran-2-one of the formula

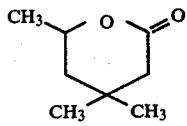

and (3) mixtures of (1) and (2), and the remainder customary constituents of perfumery compositions.

2. The perfumery composition of claim 1 wherein said trimethyl-tetrahydropyran-2-one is 4,6,6,-trimethyl-tetrahydropyran-2-one.

3. The perfumery composition of claim 1 wherein said trimethyl-tetrahydropyran-2-one is a mixture of 4,6,6-trimethyl-tetrahydropyran-2-one and 4,4,6-trimethyl-tetrahydropyran-2-one.

4. The perfumery composition of claim 3 wherein said mixture contains at least 50% by weight of 4,6,6-trimethyl-tetrahydropyran-2-one.

5. The perfumery composition of claim 3 wherein said mixture contains about 60% by weight of 4,6,6-trimethyl-tetrahydropyran-2-one and about 40% by weight of 4,4,6-trimethyl-tetrahydropyran-2-one.

6. A method of imparting a pleasing odor to a product comprising adding to said product from 0.05% to 5% by weight of the perfumery composition of claim 1.

* * * * *